United States Patent
Kaneko et al.

(10) Patent No.: US 8,649,591 B2
(45) Date of Patent: Feb. 11, 2014

(54) PATTERN INSPECTION APPARATUS AND PATTERN INSPECTION METHOD

(75) Inventors: Makoto Kaneko, Yokkaichi (JP); Takayoshi Fujii, Yokohama (JP); Yusaku Konno, Yokohama (JP); Mitsutoshi Watabiki, Yokkaichi (JP); Yusuke Ilda, Yokkaichi (JP); Shinichi Imai, Tokyo (JP); Yuichiro Yamazaki, Tokyo (JP)

(73) Assignee: Kabushiki Kaisha Toshiba, Tokyo (JP)

(*) Notice: Subject to any disclaimer, the term of this patent is extended or adjusted under 35 U.S.C. 154(b) by 150 days.

(21) Appl. No.: 13/308,719

(22) Filed: Dec. 1, 2011

(65) Prior Publication Data

US 2012/0243770 A1 Sep. 27, 2012

(30) Foreign Application Priority Data

Mar. 25, 2011 (JP) ................................. 2011-068485

(51) Int. Cl.
*G06K 9/36* (2006.01)
(52) U.S. Cl.
USPC ........................................................ 382/149
(58) Field of Classification Search
None
See application file for complete search history.

(56) References Cited

U.S. PATENT DOCUMENTS 6,867,406 B1 * 3/2005 Fairley et al. .............. 250/201.3

FOREIGN PATENT DOCUMENTS

| JP | 9-196859 | 7/1997 |
| JP | 2006-250944 A | 9/2006 |
| JP | 2007-78572 A | 3/2007 |
| WO | WO 2011-020589 A1 | 2/2011 |

OTHER PUBLICATIONS

U.S. Appl. No. 13/414,945, filed Mar. 8, 2012, Fujii, et al.
Office Action issued May 31, 2013, in Japanese Patent Application No. 2011-068485 (with English-language translation).

* cited by examiner

*Primary Examiner* — Brian P Werner
(74) *Attorney, Agent, or Firm* — Oblon, Spivak, McClelland, Maier & Neustadt, L.L.P.

(57) ABSTRACT

In accordance with an embodiment, a pattern inspection method includes: applying a light generated from a light source to the same region of a substrate in which an inspection target pattern is formed; guiding, imaging and then detecting a reflected light from the substrate, and acquiring a detection signal for each of a plurality of different wavelengths; and adding the detection signals of the different wavelengths in association with an incident position of an imaging surface to generate added image data including information on a wavelength and signal intensity, judging, by the added image data, whether the inspection target pattern has any defect, and when judging that the inspection target pattern has a defect, detecting the position of the defect in a direction perpendicular to the substrate.

20 Claims, 8 Drawing Sheets

PATTERN INSPECTION APPARATUS AND PATTERN INSPECTION METHOD

CROSS REFERENCE TO RELATED APPLICATIONS

This application is based upon and claims the benefit of priority from the prior Japanese Patent Application No. 2011-068485, filed on Mar. 25, 2011, the entire contents of which are incorporated herein by reference.

FIELD

Embodiments described herein relate generally to a pattern inspection apparatus and a pattern inspection method.

BACKGROUND

In the fields of semiconductor devices, flat panel displays, and micro electro mechanical systems (MEMS), a structure (hereinafter referred to as a "microstructure") having a micro-pattern formed on its surface is manufactured by the use of, for example, a lithography technique.

An optical inspection apparatus is used for the inspection of such a microstructure. The conventional inspection apparatus applies a light to an inspection target pattern formed on a substrate such as a wafer from, for example, a laser light source or a lamp light source, detects a reflected light from the pattern by a detector, and compares the signal intensity of the detected light by, for example, die-to-die comparison, thereby conducting a defect inspection.

Recently, patterns having high aspect ratios have been produced due to advanced miniaturization and integration of the microstructures. For example, in a trench pattern having a high aspect ratio, defects can be generated at various locations in a depth direction (see FIG. 4A).

However, there have heretofore been a problem of defect detection failures resulting from a small amount of information only obtained by the signal intensity of the detected light, and a problem of the decrease of the S/N ratio of a defect dependent on the height (depth) of the defect.

DETAILED DESCRIPTION

In accordance with an embodiment, a pattern inspection method includes: applying a light generated from a light source to the same region of a substrate in which an inspection target pattern is formed; guiding, imaging and then detecting a reflected light from the substrate, and acquiring a detection signal for each of a plurality of different wavelengths; and adding the detection signals of the different wavelengths in association with an incident position of an imaging surface to generate added image data including information on a wavelength and signal intensity, judging, by the added image data, whether the inspection target pattern has any defect, and when judging that the inspection target pattern has a defect, detecting the position of the defect in a direction perpendicular to the substrate. Embodiments will now be explained with reference to the accompanying drawings. Throughout the drawings, like components are given like reference signs, and detailed explanations of such components are omitted when not needed.

Figure 1:
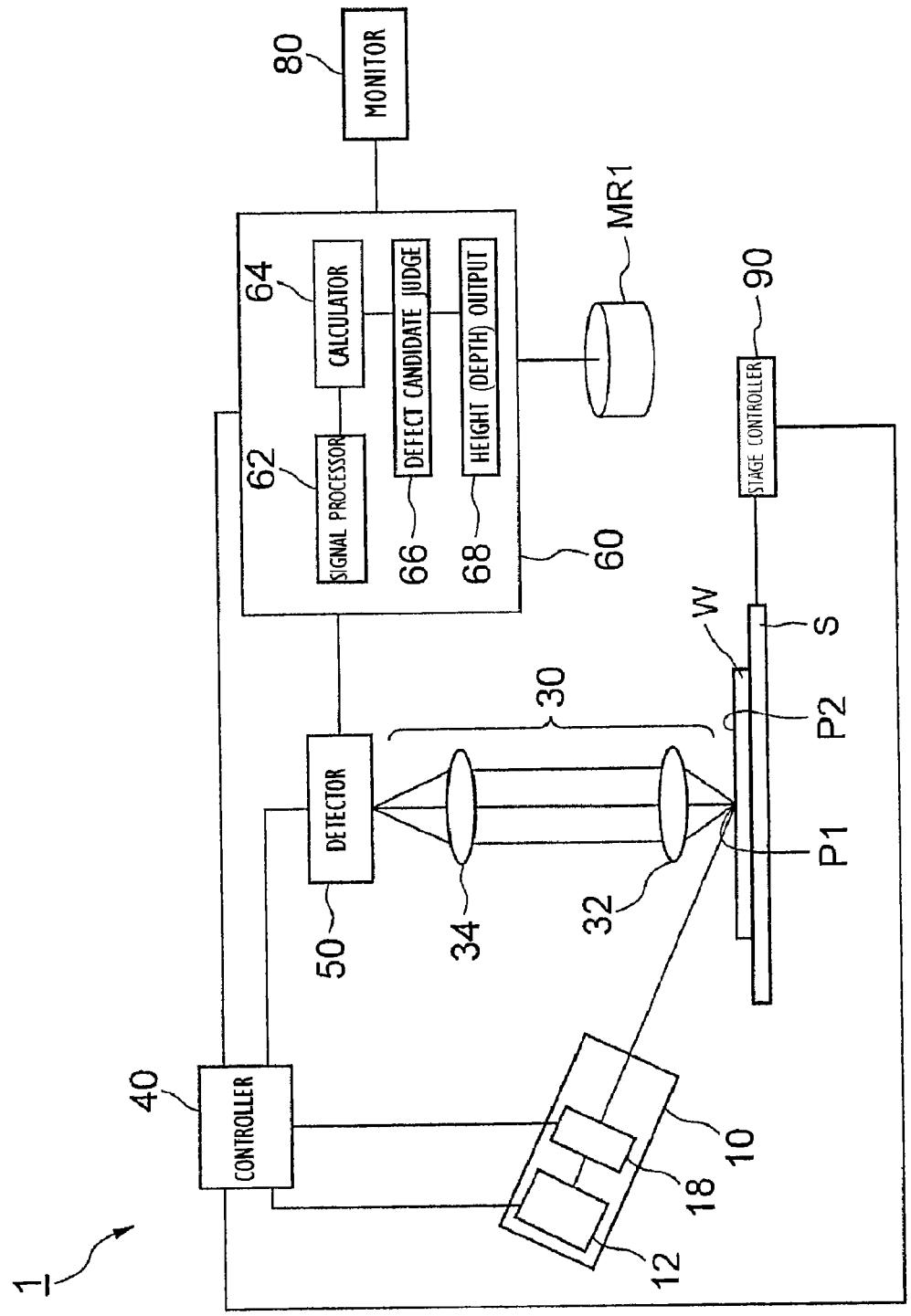
FIG. 1 is a schematic diagram illustrating the general configuration of a pattern inspection apparatus according to a first embodiment.

FIG. 1 is a schematic diagram illustrating the general configuration of a pattern inspection apparatus according to a first embodiment.

Figure 2:
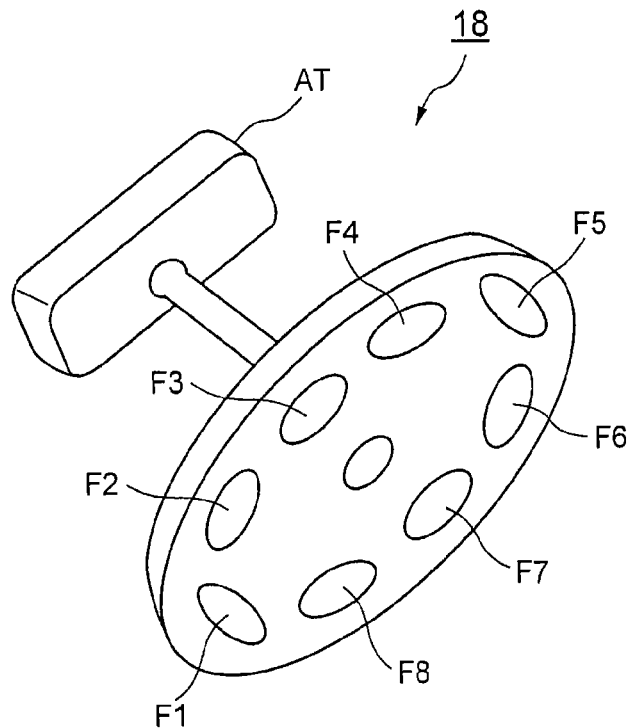
FIG. 2 is a schematic diagram illustrating a specific example of a spectroscope of the pattern inspection apparatus shown in FIG. 1.

FIG. 2 is a schematic diagram illustrating a specific example of a spectroscope of the pattern inspection apparatus shown in FIG. 1.

Figure 3:
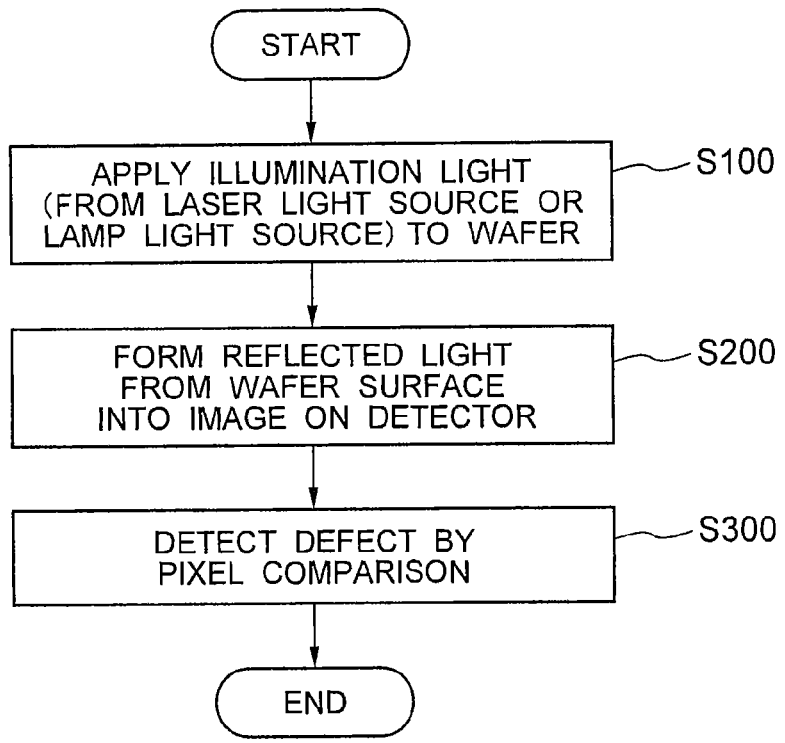
FIG. 3 is a flowchart illustrating an example of a pattern inspection method according to a comparative example.

FIG. 3 is a flowchart illustrating an example of a pattern inspection method according to a comparative example.

(1) Comparative Example

A comparative example examined by the present inventor in the process of making the invention is illustrated.

As shown in the flowchart of FIG. 3, in the pattern inspection method according to the comparative example, an illumination light from, for example, a laser light source or a lamp light source is applied to a wafer having an inspection target pattern formed therein (step S100). A reflected light from the wafer is guided and thus formed into an image on a detection surface of a detector (step S200). A detection signal is acquired by photoelectric conversion in the detector, and the intensity of the detection signal is compared pixel by pixel by, for example, die-to-die comparison, such that a defect is detected (step S300).

Recently, the aspect ratio of an inspection target pattern has been increasingly high due to more advanced miniaturization and integration of microstructures. For example, there is a trench pattern having an aspect ratio of more than 40. In such a pattern having a high aspect ratio, defects of various depths can be formed (see reference signs DF1 and DF2 in FIG. 4A). One problem associated with the pattern inspection method shown in FIG. 3 is defect detection failures because a reflected light of sufficient intensity is not returned from defects generated in the vicinity of the bottom of the trench pattern. Another problem is that the judgment of a defect is dependent on the intensity of a signal obtained by detecting a light having a single waveform, so that it is difficult to detect the height of the defect (the position of the defect in a direction perpendicular to a wafer reference surface), and the S/N ratio of the defect decreases.

(2) First Embodiment

Now, the pattern inspection apparatus according to the first embodiment is described.

First, the principle of pattern inspection on which the present embodiment is based is roughly described.

Figure 4A:
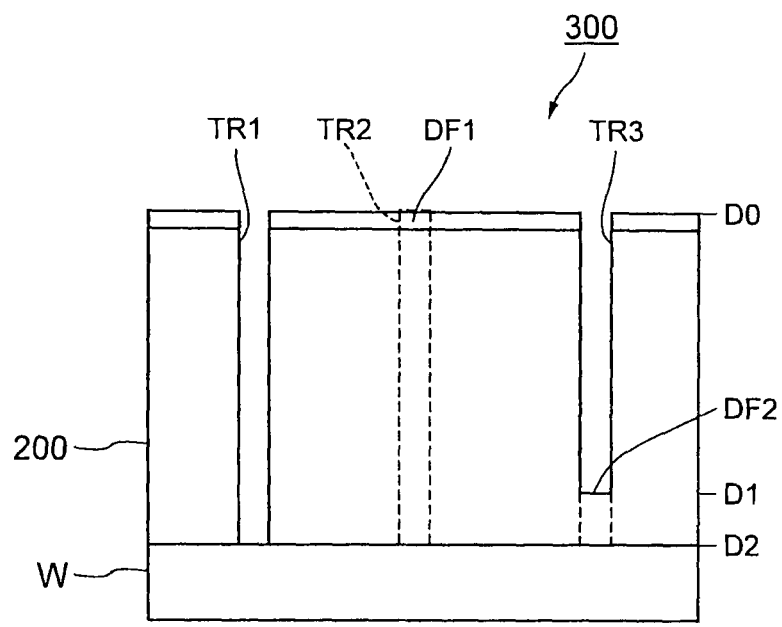
FIG. 4A is a sectional view showing an example of an inspection target pattern.

FIG. 4A is a sectional view showing an example of an inspection target pattern. FIG. 4A shows a sample 300 having trench patterns TR1 to TR3 formed therein. The trench patterns TR1 to TR3 are provided by, for example, etching to selectively remove an insulating film 200 formed on the upper surface of a wafer W. The trench pattern TR1 is a satisfactory pattern that is formed to reach the bottom surface of the insulating film 200. On the other hand, in a region where the trench pattern TR2 is to be formed, no trench pattern is formed for some reason, and the defect DF1 is generated. In the trench pattern TR3, etching is stopped in the vicinity of the bottom surface of the insulating film 200, for example, due to an impurity, and the defect DF2 having its top face located at a depth D1 is formed.

Figure 4B:
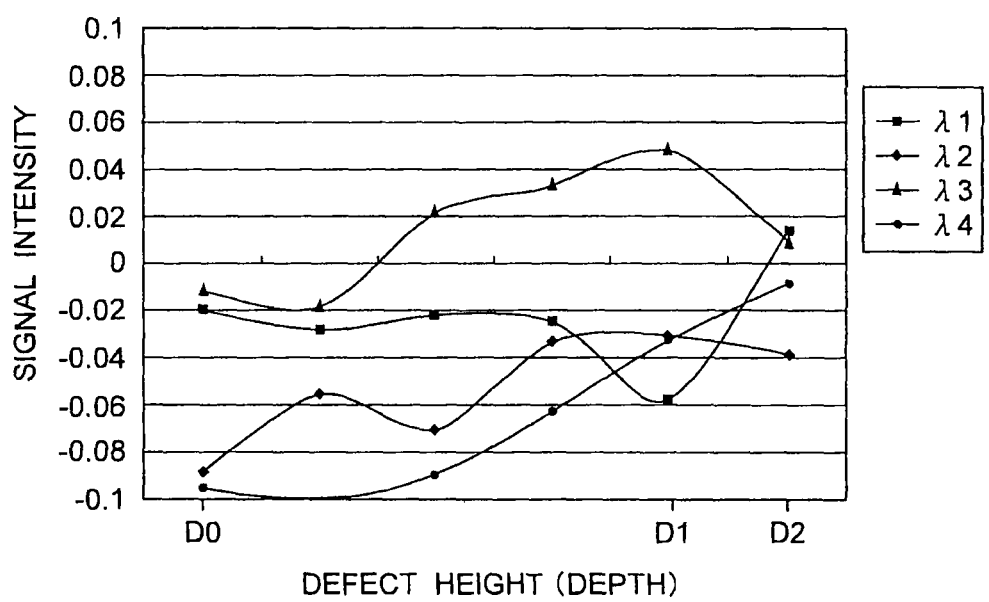
FIG. 4B is a graph illustrating the relation between defect height (depth) and signal intensity wherein spectral wavelengths are parameters.

FIG. 4B shows an example of results obtained by applying lights of a plurality of wavelengths to such a sample and detecting reflected lights therefrom. Detections of reflected lights of four wavelengths $\lambda 1$ to $\lambda 4$ from the wafer W are plotted in the graph of FIG. 4B, wherein the X-axis indicates the height (depth) of defects, and the Y-axis indicates the intensity of detection signals.

As apparent from FIGS. 4A and 4B, the reflected light of the wavelength $\lambda 2$ shows the highest signal intensity (absolute value) for the shallowest defect DF1 having a height (depth) D0. On the other hand, the reflected light of the wavelength $\lambda 1$ shows the highest signal intensity (absolute value) for the defect DF2 having a height (depth) D1 which is located in the vicinity of the bottom surface of the insulating film 200.

The relation between the heights (depths) and wavelengths of the defects is prepared as a data table to conduct pattern inspections using lights of a plurality of wavelengths, and information on the wavelengths and signal intensity of the detected defect candidates is contrasted with the data table pixel by pixel, that is, in association with the incident positions of a detection surface. This makes it possible to detect not only the position of a defect in a two-dimensional plane but also its height (depth).

A pattern inspection apparatus 1 shown in FIG. 1 is configured on the basis of such an inspection principle. The general configuration and operation of this apparatus are described below by way of example. The pattern inspection apparatus 1 shown in FIG. 1 is provided with an illumination optical system 10, an imaging optical system 30, a stage S, a stage controller 90, a controller 40, an image processor 60, and a monitor 80.

The illumination optical system 10 includes a white light source 12 and a spectroscope 18. The white light source 12 emits a broad light. The spectroscope 18 disperses the broad light into lights of a plurality of different desired wavelengths.

FIG. 2 is a schematic diagram showing an example of the specific configuration of the spectroscope 18. In the configuration shown in FIG. 2, the spectroscope 18 includes wavelength filters F1 to F8 arranged at predetermined intervals in the order of wavelengths in the peripheral region of a filter board FB, and an actuator AT for rotating the filter board FB. The wavelength filters F1 to F8 pass lights of different wavelengths therethrough. The actuator AT rotates the filter board FB in accordance with a control signal from the controller 40 to locate the wavelength filter of a desired wavelength on an optical path so that the light of the desired wavelength is applied to the wafer W. In the present embodiment, the actuator AT and the controller 40 correspond to, for example, a switching device. By providing such a switching device in the illumination optical system 10, the amount of the light applied to the wafer W can be suppressed to reduce damage to the wafer.

The illumination unit to apply lights of a plurality of different wavelengths to the wafer W is not limited to the white light source 12 and the spectroscope 18. For example, a plurality of LED light sources or laser light sources that emit lights of different wavelengths may be used, and the lights may be switched in the order of wavelengths by a light source switching device and applied accordingly.

For example, a substrate similar to the filter board shown in FIG. 2 may be used as the light source switching device. LEDs may be arranged at predetermined intervals on the periphery of the substrate, and the actuator may be used to rotate the substrate. The LED light source has the advantage of having a long life. A single laser light source that emits lights of different wavelengths may be used as an alternative illumination unit to apply lights of a plurality of different wavelengths to the wafer W.

Returning to FIG. 1, the light dispersed by the spectroscope 18 is applied to an inspection target pattern P1 formed on the wafer W. The applied light is reflected on the surface of the wafer W, and the reflected light enters the imaging optical system 30. In the present embodiment, the wafer W and the pattern P1 correspond to, for example, a substrate and a first pattern, respectively.

The imaging optical system 30 includes an objective lens 32 and an imaging lens 34. The imaging optical system 30 controls the optical path of the reflected light to form an optical image of the pattern P1 and its periphery on the detection surface of a detector 50.

The detector 50 photoelectrically converts the reflected light imaged on the detection surface, and outputs a detection signal to the image processor 60. The detector 60 comprises, for example, an infrared charge coupled device (CCD) or a photomultiplier. However, the detector is not limited to such devices. Any device that can photoelectrically convert the imaged light can be suitably selected.

The image processor 60 includes a signal processor 62, a calculator 64, a defect candidate judge 66, and a height (depth) output 68. The detection signal is provided to the signal processor 62 from the detector 50, and the signal processor 62 creates image data on the wavelength and signal intensity in association with each pixel of the detector 50. The data is provided to the calculator 64 from the signal processor 62, and the calculator 64 adds the data pixel by pixel and creates added image data on the wavelength and signal intensity associated with each pixel position. This added image data is, for example, three-dimensional data in which wavelength information is added in a z-direction to signal intensity information described in addition to (x, y) indicating the coordinate position of a pixel. In this case, the z-direction is the wavelength of the dispersed light.

The three-dimensional data thus created is stored in a memory MR1. Three-dimensional data obtained for a reference pattern is also stored in the memory MR1.

The defect candidate judge 66 compares the three-dimensional data created by the calculator 64 for the inspection target pattern P1 with the three-dimensional data for the reference pattern taken from the memory MR1, thereby judging whether the pattern P1 has any defect. More specifically, when there is data different from the three-dimensional data for the reference pattern, the defect candidate judge 66 judges that there is a defect candidate at the corresponding pixel position, that is, at a position on the wafer W that corresponds to the position at which the reflected light enters the detection surface of the detector 50.

A pattern determined to have no defect may be used as the reference pattern. However, in the present embodiment, a pattern P2 formed in an adjacent cell or die to have the same shape and dimensions as the pattern P1 is used for a defect judgment by die-to-die comparison. In the present embodiment, the pattern P2 corresponds to, for example, a second pattern.

Three-dimensional data for a defect candidate is provided to the height (depth) output 68 from the defect candidate judge 66, and the height (depth) output 68 judges the height or depth of the defect candidate by reference to the data table described above with reference to FIG. 4A that shows the relation between the wavelength, the signal intensity, and the defect height (depth).

The monitor 80 displays, for example, by a liquid crystal display, the position and height (depth) of the defect candidate judged by the image processor 60.

Here, a defect candidate judged by the defect candidate judge 66 may have, depending on its wavelength, signal intensity lower than those of other wavelengths. In this case, the defect candidate judge 66 adds a predetermined offset to the signal intensity of a desired wavelength. As a result, the defect candidate is displayed on the monitor 80 in an enhanced form.

The stage S allows the wafer W to be mounted thereon, and moves the wafer W in a direction level with the waver surface in accordance with a control signal provided from the stage controller 90. Thus, the wafer W is scanned with the illumination light in the direction level with the waver surface. The stage controller 90 generates a control signal for driving the stage 40 in accordance with a command signal from the controller 30.

The controller 40 generate various control signals, and sends the control signals to the illumination optical system 10, the stage controller 90, the detector 50, and the image processor 60. The image data is sent to the controller 40 from the image processor 60, and the controller 40 detects the sensitivity of the detector 50 for each wavelength. When judging that the sensitivity is insufficient, the controller 40 generates a control signal for correcting the sensitivity, and sends this control signal to the detector 50. This makes it possible to improve the sensitivity to, for example, a reflection signal of the wavelength λ1 shown in FIG. 4A.

Now, the pattern inspection method according to the first embodiment is described.

Figure 5:
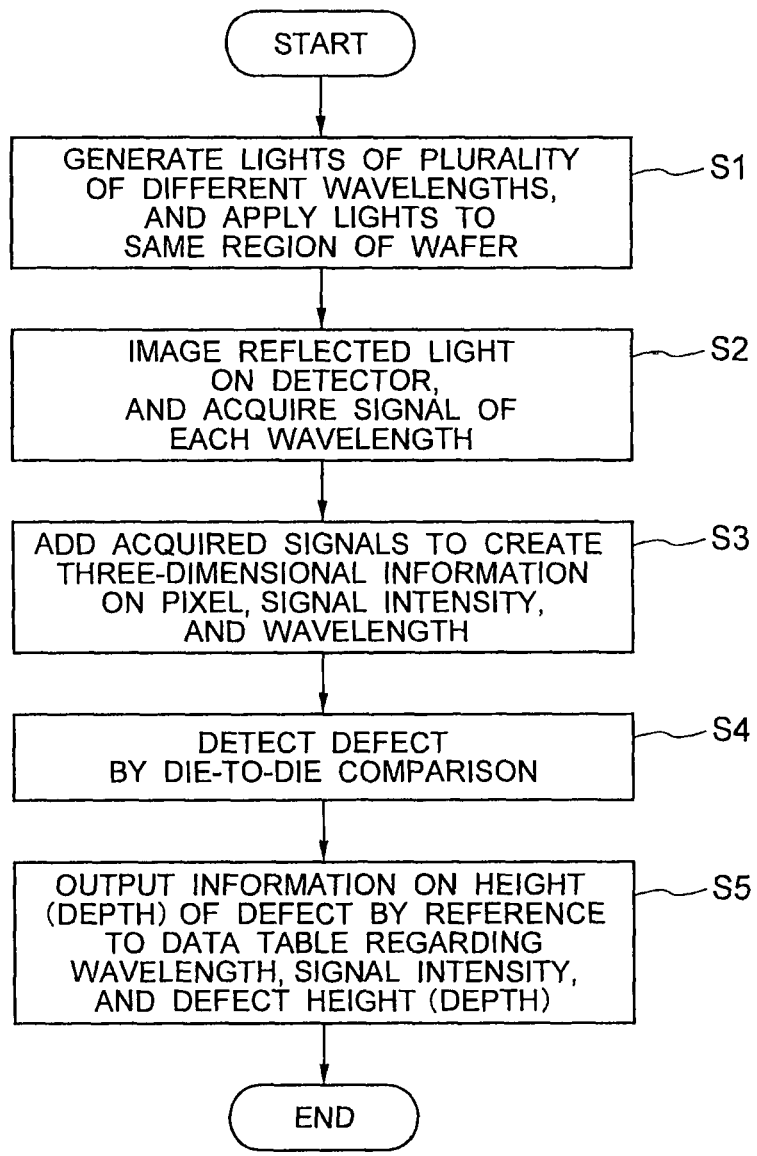
FIG. 5 is a flowchart showing an example of a pattern inspection method according to the first embodiment.

FIG. 5 is a flowchart showing an example of the pattern inspection method according to the present embodiment.

First, lights of a plurality of different wavelengths are generated, and are applied to the same region of the wafer, for example, a region where the inspection target pattern P1 is formed (step S1). The lights of a plurality of different wavelengths can be generated by, placing, on the optical path of a white light, a plurality of wavelength filters for dispersing a light into a plurality of desired wavelengths, emitting a white light from a single light source, and properly and selectively switching the wavelength filters to disperse the white light. Alternatively, a plurality of LED light sources or laser light sources that emit lights of different wavelengths can be used, and the light sources can be switched, for example, in the order of wavelengths to generate and apply lights of a plurality of different wavelengths. The lights of a plurality of different wavelengths can also be generated by turning on a signal laser light source that emits lights of different wavelengths.

Next, the reflected light from the wafer is imaged on the detection surface of the detector, and a signal of each wavelength is acquired (step S2).

Furthermore, the acquired signal is added, and three-dimensional data including information on the coordinate position (x, y) of the pixel, the signal intensity, and the wavelength is created (step S3).

The wafer is then moved to bring, into a field of view, the region, which is different from the region where the pattern P1 is formed, of the pattern P2 formed by a pattern equal in design to the pattern P1. In accordance with a procedure similar to that described above, three-dimensional data including information on the coordinate position (x, y) of the pixel, the signal intensity, and the wavelength for the pattern P2 is created. Whether the pattern P1 has any defect is detected by the comparison with the three-dimensional data, that is, by die-to-die comparison (step S4). The comparison with the three-dimensional data is not limited to the die-to-die comparison. For example, a reference pattern which has been determined in advance to have no defect may be used, and comparison may be made with three-dimensional data obtained for the reference pattern.

Finally, when the pattern P1 is judged to be a defect candidate, information on the height or depth of the defect candidate is output by reference to the prepared data table that shows the relation between the wavelength, the signal intensity, and the defect height (depth) (step S5).

Thus, according to the present embodiment, three-dimensional data including information on the coordinate position (x, y) of the pixel, the signal intensity, and the wavelength is created, so that the information amount is much greater than in the comparative example, and defect detection failures can therefore be inhibited. Moreover, reference is made to the data table that shows the relation between the wavelength, the signal intensity, and the defect height (depth). Therefore, it is possible to acquire not only information on the presence of a defect but also information on the height or depth of the defect, so that the S/N ratio of the defect advantageously improves independent of the height (depth) of the defect.

(3) Second Embodiment

Figure 6:
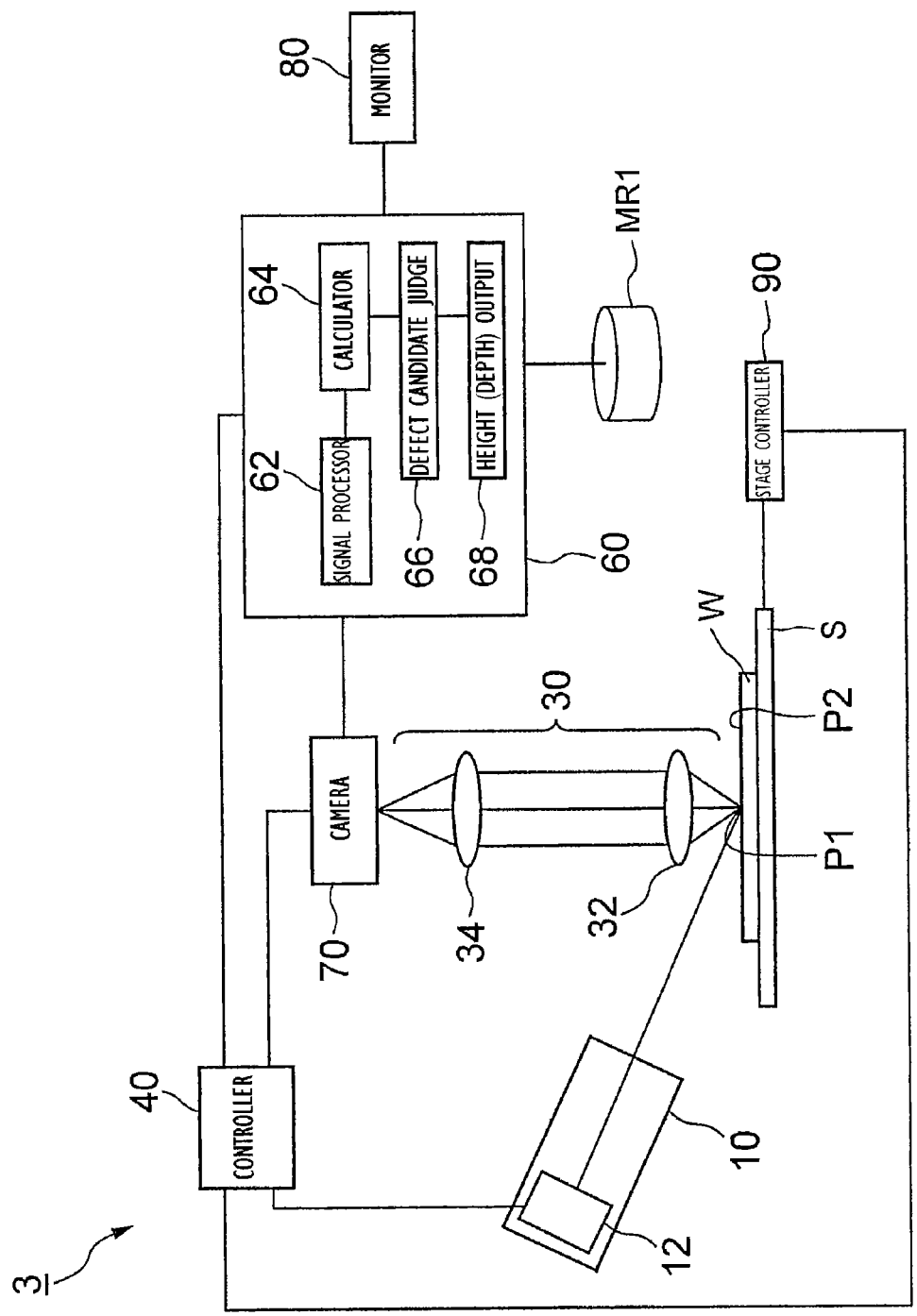
FIG. 6 is a schematic diagram illustrating the general configuration of a pattern inspection apparatus according to a second embodiment.

Now, a pattern inspection apparatus according to the second embodiment is shown by way of example with reference to FIG. 6.

FIG. 6 is a schematic diagram illustrating the general configuration of the pattern inspection apparatus according to the present embodiment.

As obvious from the contrast with FIG. 1, a pattern inspection apparatus 3 shown in FIG. 6 is not provided with a spectroscope 18, and is provided with a color CCD camera 70 as a detector.

According to this configuration, detection signals of a plurality of different wavelengths can also be acquired by imaging a reflected light from a wafer W on the detection surface of the color CCD camera 70.

The configuration of the pattern inspection apparatus 3 shown in FIG. 6 is substantially the same in other respects as the configuration of the pattern inspection apparatus 1 shown in FIG. 1. Therefore, the operation of the pattern inspection apparatus 3 is also substantially the same as the operation of the pattern inspection apparatus 1 except for the spectral process. Accordingly, detailed explanations are not given.

Thus, as a means of acquiring detection signals of a plurality of different wavelengths without dispersing an incident light, a prism is provided, for example, between an objective lens 32 and an imaging lens 34 in an imaging optical system 30 to divide an optical path into a plurality of optical paths, and a desired wavelength filter is disposed for each of the divided optical paths. In this way, detection signals of a plurality of different wavelengths can also be acquired by a detector similar to the detector 50 in FIG. 1. In this case, the prism corresponds to, for example, optical path divider.

As another means of acquiring detection signals of a plurality of different wavelengths, a spectroscope may be configured by an actuator and by a filter board in which wavelength filters of desired wavelengths are arranged on its periphery in the same manner as the spectroscope 18 shown in FIG. 2. This spectroscope is disposed, for example, between the objective lens 32 and the imaging lens 34. The filter board FB is rotated by the actuator AT to locate the wavelength filter of a desired wavelength on the optical path of the reflected light so that the light of the desired wavelength enters the detection surface of the detector 50. The actuator AT can be operated in accordance with a control signal from the controller 40 as in the first embodiment. In this case, the spectroscope disposed between the objective lens 32 and the imaging lens 34 corresponds to, for example, switching devices Now, a pattern inspection method according to the second embodiment is described.

Figure 7:
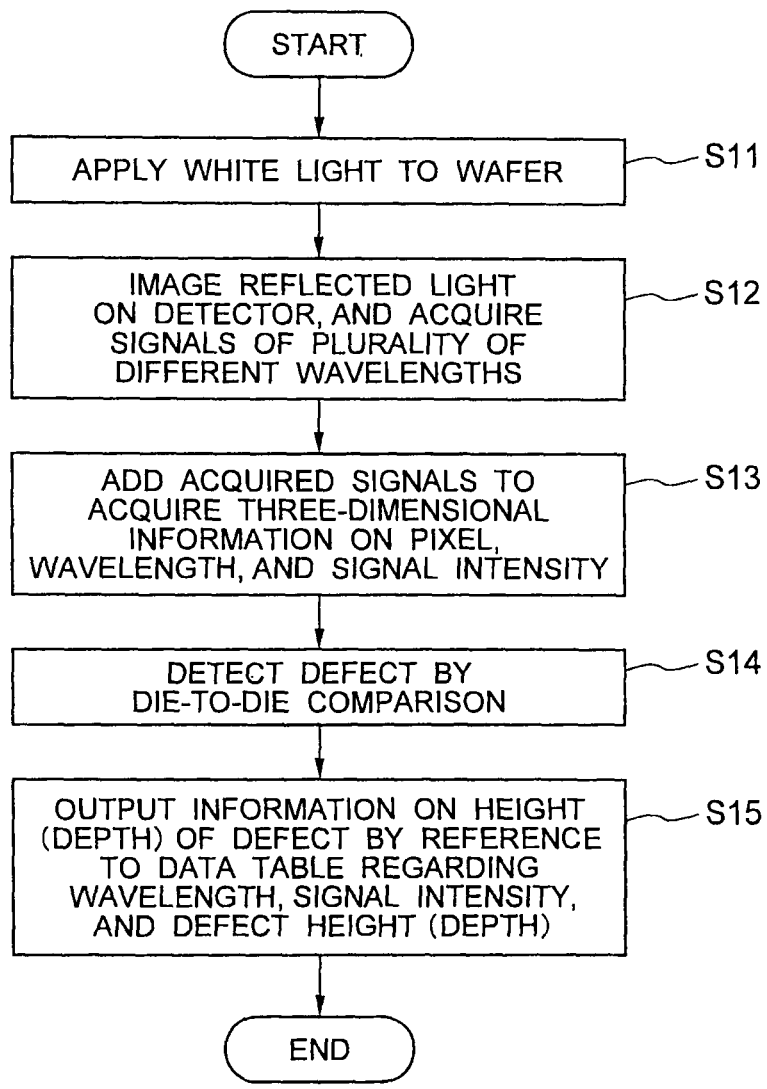
FIG. 7 is a flowchart showing an example of a pattern inspection method according to the second embodiment.

FIG. 7 is a flowchart showing an example of the pattern inspection method according to the second embodiment.

First, a white light is generated from a light source, and applied to the same region of the wafer, for example, a region where an inspection target pattern P1 is formed (step S11).

Next, the reflected light from the wafer is imaged on the detection surface of the detector, and a signal of each wavelength is acquired (step S12).

In order to acquire signals of a plurality of different wavelengths, a color CCD camera may be used as a detector, or a prism for dispersing the reflected light may be provided in the imaging optical system 30 and a plurality of desired wavelength filters may be disposed on the optical path of each dispersed light. Alternatively, in order to acquire signals of a plurality of different wavelengths, a filter board having a wavelength filter of a desired wavelength disposed therein may be disposed, for example, between the objective lens 32 and the imaging lens 34, and the board FB may be rotated to locate the wavelength filter of a desired wavelength on the optical path of the reflected light so that the light of the desired wavelength enters the detection surface of the detector Furthermore, the acquired signal is added, and three-dimensional data including information on the coordinate position (x, y) of the pixel, the signal intensity, and the wavelength is created (step S13).

The wafer is then moved to bring, into a field of view, the region, which is different from the region where the pattern P1 is formed, of a pattern P2 formed by a pattern equal in design to the pattern P1. In accordance with a procedure similar to that described above, three-dimensional data for the pattern P2 including information on the coordinate position (x, y) of the pixel, the signal intensity, and the wavelength is created. Whether the pattern P1 has any defect is detected by the comparison with the created three-dimensional data for the pattern P2, that is, by die-to-die comparison (step S14). The comparison with the three-dimensional data is not limited to the die-to-die comparison. For example, a reference pattern which has been determined in advance to have no defect may be used, and comparison may be made with three-dimensional data obtained for the reference pattern.

Finally, when the pattern P1 is judged to be a defect candidate, information on the height or depth of the defect candidate is output by reference to the prepared data table that shows the relation between the wavelength, the signal intensity, and the defect height (depth) (step S15).

Thus, according to the present embodiment as well, three-dimensional data including information on the coordinate position (x, y) of the pixel, the signal intensity, and the wavelength is created, so that the information amount is much greater than in the comparative example, and defect detection failures can therefore be inhibited. Moreover, reference is made to the data table that shows the relation between the wavelength, the signal intensity, and the defect height (depth). Therefore, it is possible to acquire not only information on the presence of a defect but also information on the height or depth of the defect, so that the S/N ratio of the defect advantageously improves independent of the height (depth) of the defect.

(4) Avoidance of Noise Resulting from Thin Film Thickness Variation

In a pattern inspection targeted at a pattern formed by a thin film, light interference caused by the thickness variation of thin films results in noise. To avoid this, the light from the light source of the pattern inspection apparatus preferably has a wavelength width that can cancel the thickness variation. More specifically, a light source having a wavelength width of ±20 nm or more is preferable. To this end, it is possible to use, for example, a pulse laser of triple harmonic by Ti: sapphire and of a femtosecond order (10 to 15) having a wavelength of 260 nm±20 nm.

Figure 8:
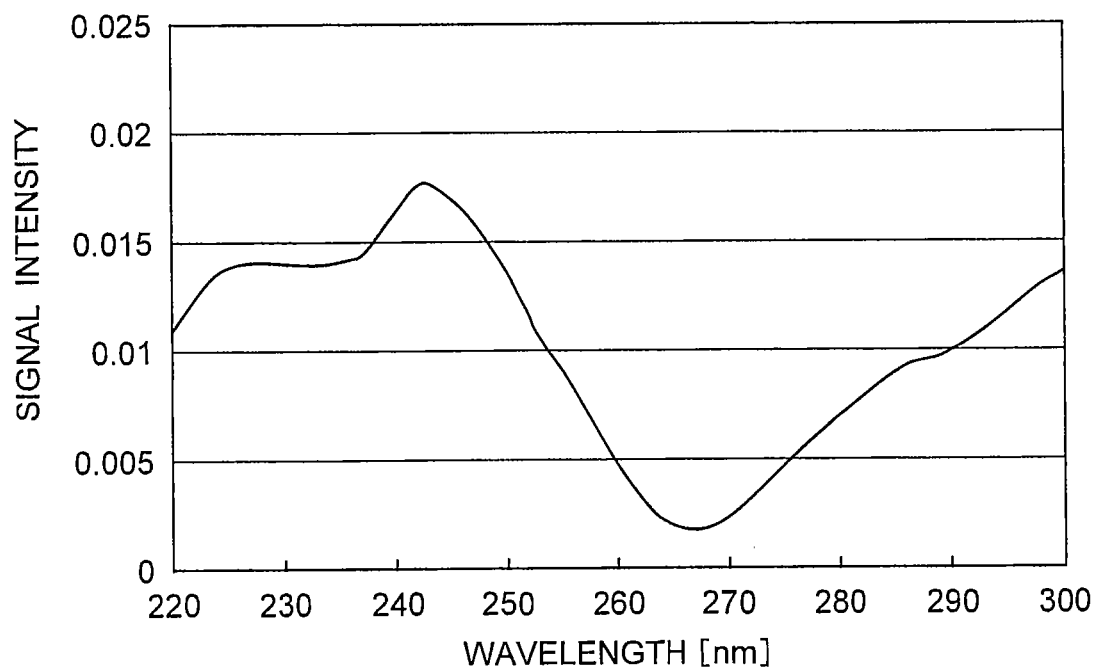
FIG. 8 is a graph showing an example of the wavelength dependence of reflectance from a given defect, obtained by the pattern inspection apparatus shown in FIG. 1.

FIG. 8 is a graph in which the wavelength dependence of reflectance from a given defect is found by a simulation in the pattern inspection apparatus shown in FIG. 1. Reflectance greatly changes with the wavelength due to thin film interference. Therefore, in the example shown in FIG. 8, reflectance decreases in the vicinity of a wavelength of 260 nm. This proves that sufficient sensitivity is not obtained by the normal laser of a single waveform. Accordingly, if a pulse laser light source having a wavelength of 260 nm±20 nm is used instead of the white light source 12 in the pattern inspection apparatus shown in FIG. 1, the average of the integrated intensity of the reflectance variation in FIG. 8 becomes signal intensity. This enables a robust pattern inspection that copes with the thickness variation.

Moreover, a broadband light source which is a combination of lasers of a plurality of different wavelengths can be used instead of the pulse laser light source.

Figure 9:
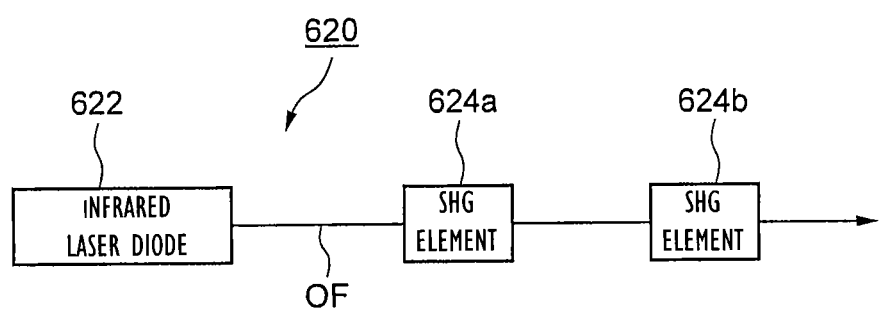
FIG. 9 is a schematic diagram illustrating a basic light source unit for generating a deep ultraviolet light.

FIG. 9 is a schematic diagram illustrating a basic light source unit for generating a deep ultraviolet light.

A basic light source unit 620 shown in FIG. 9 includes an infrared laser diode 622, and second harmonic generation (SHG) elements 624a and 624b connected in series. An optical fiber OF optically connects the infrared laser diode 622 and the SHG element 624a, and the SHG element 624a and the SHG element 624b. The infrared laser diode 622 emits infrared laser having a wavelength of 1064 nm±0.25 nm. This infrared laser is used by the SHG elements 624a and 624b to generate a quad harmonic, and a deep ultraviolet light is output from the SHG element 624b.

The relation between the wavelength and the wavelength width is:

$$\Delta\lambda = \Delta\lambda 266 \text{ nm} \times (\lambda 266 \text{ nm}/\lambda 1064 \text{ nm})^2.$$

Therefore, the deep ultraviolet light output from the SHG element 624b has a wavelength width of about 266 nm±1.25 pm.

Figure 10A:
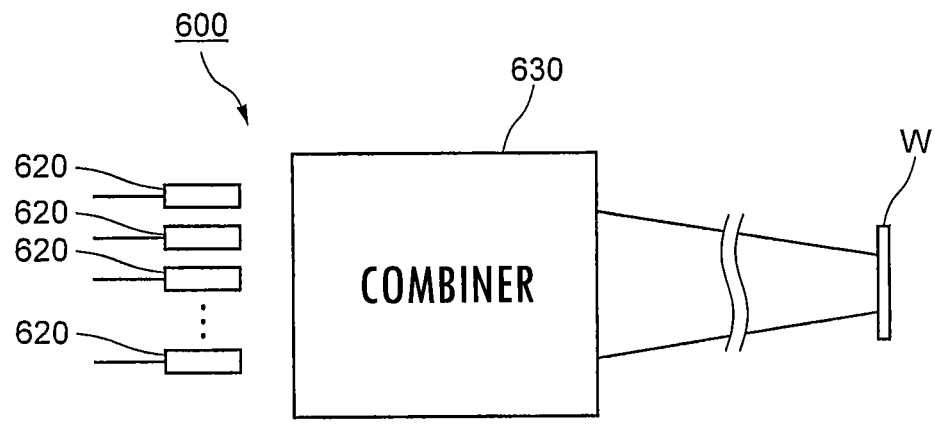
FIGS. 10A and 10B are schematic diagrams illustrating broadband light sources that use the basic light source units shown in FIG. 9.
Figure 10B:
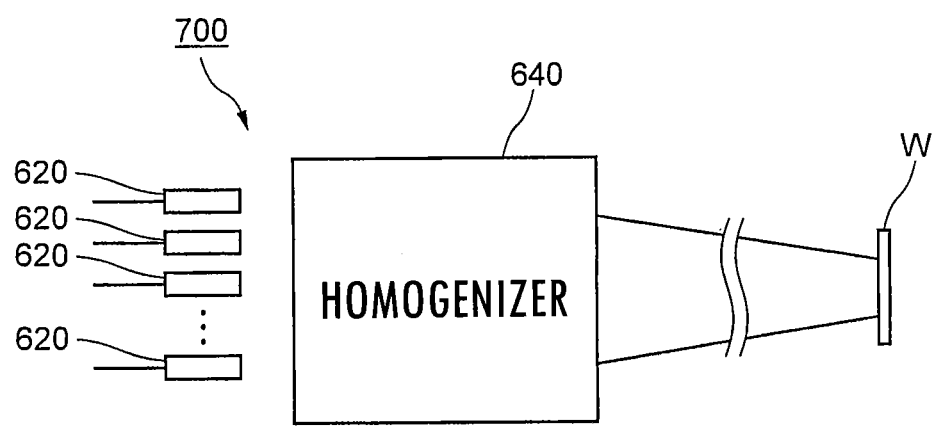

FIGS. 10A and 10B are schematic diagrams illustrating broadband light sources configured by using the basic light source units 620 shown in FIG. 9.

A broadband light source 600 shown in FIG. 10A comprises 100 basic light source units 620 and a combiner 630. The central wavelengths of the basic light source units 620 are different from one another due to temperature control. Deep ultraviolet lights having different central wavelengths are combined together by the combiner 630 to obtain a light source of a desired wavelength width. The broadband light source 600 in this example makes it possible to obtain a light source having a wavelength width of ±1.5 nm. It should be understood that the light source is not limited to this wavelength width. A light source of a desired wavelength width can be obtained by controlling the central wavelength of the original emitted light of the infrared laser diode 622 and the number of the basic light source units 620.

A broadband light source 700 shown in FIG. 10B comprises 100 basic light source units 620 and a homogenizer 640. The homogenizer 640 homogenizes nonuniform light intensity distributions of the deep ultraviolet lights having different central wavelengths output from the 100 basic light source units 620. More specifically, as the homogenizer 640, it is possible to use arrayed lenses that bend a light by refraction, and also use a diffractive optical element (DOE) to control a wave front by diffracted light. In the present embodiment, the homogenizer 640 corresponds to, for example, a wave front homogenizing optical system.

In the embodiments described above, not only the single light source but also a plurality of light sources may be used. In this case as well, the above-mentioned pulse laser light source or broadband light source is applicable to each of the above-mentioned light sources.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A pattern inspection apparatus comprising:
a light source unit configured to generate and emit lights having different wavelengths;
an illumination unit configured to apply the lights of the different wavelengths from the light source unit to the same region of a substrate in which an inspection target pattern is formed;
a detection unit configured to detect reflected lights of a plurality of different wavelengths reflected by the substrate and then output a signal for each wavelength;
an imaging unit configured to guide the reflected lights into the detection unit, and image the reflected lights on a detection surface of the detection unit; and
an image processing unit configured to add the signal for each wavelength in association with an incident position of the detection surface to generate added image data comprising information on a wavelength and signal intensity, judging, by the added image data, whether the inspection target pattern has any defect, and when judging that the inspection target pattern has a defect, detecting the position of the defect in a direction perpendicular to the substrate.

2. The apparatus of claim 1,
wherein the light source unit comprises a single light source, a plurality of wavelength filters configured to disperse a light from the light source into a plurality of wavelengths, and a switching device configured to selectively switch the wavelength filters to locate the wavelength filters on an optical path of the light emitted from the light source.

3. The apparatus of claim 2,
wherein each light source is a broadband light source configured to emit a combination of a plurality of lasers having a central wavelength width of ±10 pm or less and having different central wavelengths.

4. The apparatus of claim 1,
wherein the light source unit comprises a plurality of LED light sources or laser light sources configured to emit lights of different wavelengths, and a light source switching device configured to selectively switch the LED light sources or laser light sources.

5. The apparatus of claim 1,
wherein the light source unit comprises a single laser light source configured to emit lights of different wavelengths.

6. A pattern inspection apparatus comprising:
a light source;
an illumination unit configured to apply a light generated from the light source to a substrate in which an inspection target pattern is formed;
a detection unit configured to detect lights of a plurality of different wavelengths reflected from the substrate and then output detection signals of different wavelengths;
an imaging unit configured to guide the reflected lights into the detection unit, and imaging the reflected lights on a detection surface of the detection unit; and
an image processing unit configured to add the detection signals of the different wavelengths in association with an incident position of the detection surface to generate added image data comprising information on a wavelength and signal intensity, judging, by the added image data, whether the inspection target pattern has any defect, and when judging that the inspection target pattern has a defect, detecting the position of the defect in a direction perpendicular to the substrate.

7. The apparatus of claim 6,
wherein each light source emits a pulse laser having a wavelength width of ±40 nm.

8. The apparatus of claim 6,
wherein each light source is a broadband light source configured to emit a combination of a plurality of lasers having a central wavelength width of ±10 pm or less and having different central wavelengths.

9. The apparatus of claim 8,
wherein each light source comprises a wave front homogenizing optical system configured to homogenize light intensity distributions of the lasers.

10. The apparatus of claim 6,
wherein the light source is a single light source configured to emit a white light, and
the detection unit comprises a color CCD camera configured to output a detection signal for each of the lights of the different wavelengths.

11. The apparatus of claim 6,
wherein the light source is a single light source configured to emit a white light, and the imaging unit comprises an optical path divider configured to divide the reflected light from the substrate to generate a plurality of lights, and a plurality of wavelength filters arranged on optical paths of the lights obtained by dividing the reflected light.

12. The apparatus of claim 6,
wherein the light source is a single light source configured to emit a white light, and
the imaging unit comprises a plurality of wavelength filters configured to disperse the reflected light into a plurality of desired wavelengths, and a switching device configured to selectively switch the wavelength filters to locate the wavelength filters on an optical path of the reflected light.

13. The apparatus of claim 6,
wherein the inspection target pattern comprises a first pattern, and a second pattern formed in a region different from a region where the first pattern is formed, the second pattern being equal in design to the first pattern, and
the image processing unit respectively generates first and second added image data for the first and second patterns, and compares the first and second added image data in association with the incident position of the detection surface to judge whether the defect is present.

14. The apparatus of claim 6,
wherein when a defect is detected, the image processing unit judges the position of the defect in the direction perpendicular to the substrate by reference to a data table showing the relation between a wavelength, the intensity of a detection signal, and the position of the defect in the direction perpendicular to the substrate.

15. The apparatus of claim 6,
wherein the image processing unit adds an offset to the signal intensity of each desired wavelength to enhance a defect.

16. The apparatus of claim 6, further comprising
a sensitivity correcting unit configured to correcting the sensitivity of the detection unit for each wavelength.

17. A pattern inspection method comprising:
applying a light generated from a light source to the same region of a substrate in which an inspection target pattern is formed;
guiding, imaging and then detecting a reflected light from the substrate, and acquiring a detection signal for each of a plurality of different wavelengths; and
adding the detection signals of the different wavelengths in association with an incident position of an imaging surface to generate added image data comprising information on a wavelength and signal intensity, judging, by the added image data, whether the inspection target pattern has any defect, and when judging that the inspection target pattern has a defect, detecting the position of the defect in a direction perpendicular to the substrate.

18. The method of claim 17,
wherein the signals of the different wavelengths are acquired by
dispersing the light generated from the light source into lights of the different wavelengths,
applying the dispersed lights of the different wavelengths to the same region of the substrate, and
guiding, imaging and then detecting reflected lights of a plurality of different wavelengths reflected by the substrate.

19. The method of claim 17,
wherein the signals of the different wavelengths are acquired by
dispersing the reflected light into lights of different wavelengths, and
imaging the dispersed lights of the different wavelengths.

20. The method of claim 17,
wherein the position of the defect in the direction perpendicular to the substrate is judged by reference to a data table showing the relation between a wavelength, the intensity of a detection signal, and the position of the defect in the direction perpendicular to the substrate.

* * * * *